United States Patent
Samain et al.

(10) Patent No.: US 6,524,596 B1
(45) Date of Patent: Feb. 25, 2003

(54) COSMETIC COMPOSITION CONTAINING AN AQUEOUS DISPERSION OF INSOLUBLE POLYMER MATERIAL PARTICLES, USE AND METHOD

(75) Inventors: Henri Samain, Bièvres (FR); Christine Dupuis, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/622,078

(22) PCT Filed: Dec. 23, 1998

(86) PCT No.: PCT/FR98/02862

§ 371 (c)(1),
(2), (4) Date: Nov. 1, 2000

(87) PCT Pub. No.: WO99/40889

PCT Pub. Date: Aug. 19, 1999

(30) Foreign Application Priority Data

Feb. 13, 1998 (FR) ............................................. 98 01773

(51) Int. Cl.⁷ ........................... A61K 7/06; A61K 7/11; A61K 9/10; A61K 9/12; B01F 3/12
(52) U.S. Cl. ........................... 424/401; 424/47; 424/70; 424/485; 424/487; 424/43; 424/70.12; 424/DIG. 1; 514/937; 514/944
(58) Field of Search ................................ 424/401, 47, 70, 424/485, 487, 43, 70.12, DIG. 1; 514/937, 944

(56) References Cited

U.S. PATENT DOCUMENTS

| | | | | |
|---|---|---|---|---|
| 4,196,190 A | * | 4/1980 | Geman et al. ................. 424/47 |
| 4,543,249 A | * | 9/1985 | Nelson ......................... 424/70 |
| 6,071,499 A | * | 6/2000 | Dupuis ......................... 424/47 |
| 6,083,494 A | * | 7/2000 | Samain et al. ............ 424/70.11 |
| 6,126,921 A | * | 10/2000 | Emmerling et al. .......... 424/47 |
| 6,165,446 A | * | 12/2000 | Samain et al. .............. 424/401 |
| 6,173,907 B1 | * | 1/2001 | Benoist .................... 222/402.1 |
| 6,368,606 B1 | * | 4/2002 | Dubief et al. ................ 424/401 |

FOREIGN PATENT DOCUMENTS

| | | | |
|---|---|---|---|
| EP | 0 688 557 | | 12/1995 |
| FR | 2 737 658 | | 2/1997 |
| FR | 2 737 659 | | 2/1997 |
| FR | 2 737 660 | | 2/1997 |
| FR | 2 740 033 | | 4/1997 |
| FR | WO 97/47535 | * | 12/1997 |
| JP | 409118603 A | * | 5/1997 |
| WO | WO 95/28908 | | 11/1995 |
| WO | WO 95/28909 | | 11/1995 |

OTHER PUBLICATIONS

JP–409118603 A, Dupuis, Christine, Cosmetic Composition Having Fixing and/or Conditioning Power and Containing Specific Acrylic Polymer, May 06, 1997, abstract.*
English language Derwent Abstract of FR 2 737 658.
English language Derwent Abstract of FR 2 737 659.
English language Derwent Abstract of FR 2 737 660.
English language Derwent Abstract of FR 2 740 033.

* cited by examiner

*Primary Examiner*—Frederick Krass
*Assistant Examiner*—Clinton Ostrup
(74) *Attorney, Agent, or Firm*—Finnegan, Henderson, Farabow, Garrett & Dunner, L.L.P.

(57) ABSTRACT

The invention concerns a cosmetic composition comprising in a cosmetically acceptable aqueous or hydroalcoholic medium, an aqueous dispersion of insoluble styling polymer particles, resulting in a mean fixing energy of styling material after drying on the keratinous fibers less than 200 microjoules in a fixing test. The invention is applicable to hair lacquers.

19 Claims, No Drawings

COSMETIC COMPOSITION CONTAINING AN AQUEOUS DISPERSION OF INSOLUBLE POLYMER MATERIAL PARTICLES, USE AND METHOD

This application is a national stage application, filed under 35 U.S.C. 371 of PCT/FR98/02862, filed Dec. 23, 1998.

The invention relates, in general, to an aqueous or aqueous-alcoholic cosmetic composition containing an aqueous dispersion of insoluble particles of fixing polymer, in particular for the treatment of keratinous fibres.

For ecological and legislative reasons, for many years, a very special interest has been expressed in the production of essentially aqueous cosmetic hair compositions. Now, the use of water-soluble polymers poses problems of viscosity for the compositions. For this reason, the use of aqueous dispersions of insoluble particles of polymers in aqueous or aqueous-alcoholic cosmetic compositions has proved particularly advantageous. In addition, aqueous dispersions of insoluble particles of polymer material (latex) make it possible to obtain a more rapid drying time for aqueous or aqueous-alcoholic cosmetic compositions.

Such cosmetic compositions comprising an aqueous dispersion of polymer material are described in numerous documents, such as the French patents and patent applications in the name of the company L'OREAL No. 95 09772 (cosmetic composition comprising an aqueous dispersion of nonionic polymer), No. 95 12235 (cosmetic composition comprising a graft silicone polymer and an aqueous dispersion of nonionic or cationic polymer), No. 95 09773 (cosmetic composition containing an aqueous dispersion of polymer and an insoluble silicone), International Applications WO 95/28908 and WO 95/28909 (composition comprising an aqueous dispersion of insoluble polymer and a water-soluble polymer and composition containing an aqueous dispersion of insoluble polymer), and the document EP-0,688,557 (composition for treating hair, comprising a water-soluble polymer and an aqueous dispersion of an insoluble polymer).

However, the use of the aqueous dispersions of insoluble polymers or latex has two disadvantages:
- their removal with the aid of a shampoo is sometimes difficult because of their resistance to water; and
- their removal during brushing is also often difficult.

Indeed, the latexes often leave, after entanglement, small fragments of film or residues which remain stuck to the hair and damage the good cosmetic performance of the composition (disentanglement, soft and natural touch), in particular of lacquers.

Although the addition of water-soluble polymers to the compositions containing aqueous dispersions of insoluble polymers partially overcomes the problems of the removal with shampoos, the problem of their removal by brushing remains.

Now, the applicant has discovered, surprisingly, that by using, in particular for the retention and/or the fixing of the hairstyle, aqueous or aqueous-alcoholic cosmetic compositions comprising an aqueous dispersion of insoluble particles of fixing polymer, leading to defined properties of sticking to the hair, it was possible to obtain the desired hairstyle retention performance while avoiding the drawbacks of removal during brushing and of residues mentioned above.

The subject of the present invention is therefore an aqueous or aqueous-alcoholic cosmetic composition, in particular a cosmetic composition for the retention of the hairstyle, containing, in a cosmetically acceptable medium, an aqueous dispersion of insoluble particles of fixing polymer, the aqueous composition being such that the energy for the sticking of the material resulting from drying to the keratinous fibre is on average less than 200 microjoules in the test of sticking after drying defined below, and preferably less than 100 $\mu J$.

Preferably, additionally, the composition is such that the percentage of keratinous fibres leading to a material resulting from drying-fibre sticking energy greater than 200 $\mu J$ in the sticking test is less than 15%.

In the context of the present application, "cosmetic composition for the retention of the hairstyle" is understood to mean any composition whose function is to temporarily fix the shape of the hairstyle, such as for example hair-styling lacquers and sprays, hair-styling gels and mousses.

"Fixing power of the composition" designates the capacity of the latter to give cohesion to the hair such that the initial shaping of the hairstyle is retained.

"Fixing polymer" is understood to mean any polymer whose function is to fix the shape of the hairstyle.

According to the present invention, "keratinous fibres" is understood to mean the hair, the eyelashes, the eyebrows and more particularly the hair.

The energy for the sticking of the keratinous fibre to the material resulting from drying is defined as being the energy, in the test described below, at which the keratinous fibre separates from the material or at which the material breaks.

The sticking test according to the invention is described in relation to FIG. 1 which schematically represents a test sample.

To produce a sample for the sticking test according to the invention, the first step consists in pasting an eyelet 2 in the top portion of a glass slide 1. There are then deposited inside the hole 3 of the eyelet, which has a diameter of 3 mm, 4 $\mu l$ of a composition containing at least one aqueous dispersion of insoluble particles of polymer.

Immediately after depositing the drop of composition to be tested, a previously calibrated keratinous fibre (about 90 $\mu$ in diameter) is placed on it.

The fibres are previously all oriented in the same direction, namely in the root-tip direction.

At least 30 sample slides are used so as to have a sampling which is as representative as possible.

The slides are then allowed to dry in a conditioned room for 12 hours.

The determination of the sticking of the fixing material/keratinous fibre is carried out on 30 samples using an extensometer of the INSTRON 1122 or LLOYD type, controlled by a computerized system.

In this test, the glass slide is kept in place by the lower jaw and the keratinous fibre is held firmly at 8 mm from the top edge of the bonding by the movable upper jaw of the extensometer. The pulling rate used is 10 mm/minute, and the measurements are made at 22° C.±2° C. and in an atmosphere having a relative humidity of 43%±3%.

This test demonstrated two main types of individual behaviour.

In a first behaviour, the keratinous fibre detaches sufficiently easily from the material without an elastic deformation of the fibre being observed with the aid of a microscope.

In this first behaviour, the energy for the sticking of the material to the keratinous fibre is less than 200 microjoules.

In a second mode of behaviour, the keratinous fibre detaches with a sticking energy greater than 200 microjoules and with a high level of elastic deformation of the keratinous fibre.

By applying this test to the different fixing materials resulting from the application of compositions containing at least one aqueous dispersion of insoluble particles of polymer, it is possible to select cosmetic compositions, in particular cosmetic compositions for the retention of the hairstyle, having the desired properties, in particular allowing easy removal of the final material by brushing.

Among the polymers which are suitable for the aqueous dispersions of insoluble particles of polymer material according to the invention, there may be mentioned (meth) acrylic polymers, polyesters, polyurethanes, polyethers, polyvinyls, polyolefins, polystyrenes, mixtures of these polymers with each other or with other polymers, in particular silicones, provided that the compositions containing these dispersions satisfy the conditions mentioned above.

Generally, the materials resulting from the compositions according to the invention have a glass transition temperature of between 20 and 40° C., which can be optionally obtained by plasticization.

In general, the concentration of active material in the aqueous dispersion according to the invention is between 0.1 and 25% by weight.

As is well known, the aqueous dispersions of polymers according to the invention can be obtained by polymerization or copolymerization in suspension or in emulsion of monomers (such dispersions are also known by the name latex). Pseudolatexes can also be used.

By way of example, the aqueous dispersions which are suitable in the present invention can result in particular from the polymerization or from the copolymerization of monomers such as for example styrene, butadiene, ethylene, propylene, vinyltoluene, vinyl propionate, vinyl alcohol, acrylonitrile, chloroprene, vinyl acetate, urethanes, isoprene, isobutene and esters or amides of acrylic or methacrylic, maleic, crotonic or itaconic acids, vinyl ether, vinylpyrrolidone or vinyl imidazole.

The aqueous dispersions which can be used according to the invention may also result from the condensation of ionic or nonionic monomers leading to polymers such as polyesters, polyamides, polyurethanes or polyethers.

For further information relating to the aqueous dispersions of polymers which are suitable for he compositions of the present invention, reference may be made to the previously cited prior art documents. However, it should be noted that among the polymers which are described in this prior art, it is advisable to determine those which, alone or in the form of a mixture with other polymers or particular adjuvants such as silicones, lead to compositions which satisfy the above test.

A class of aqueous dispersions recommended for the compositions of the present invention are the aqueous dispersions of (meth)acrylic copolymers, in particular ethyl acrylate/methyl methacrylate/-methacrylic acid/acrylic acid copolymers.

The aqueous dispersions useful in the compositions of the present invention may, as indicated above, comprise other polymers, in particular silicones, as long as the resulting composition satisfies the conditions of the above test.

Thus, according to the present invention, it is possible to use any silicone known per se, whether it is an oil, a resin or alternatively a silicone gum. Silicones are organosilicon oligomers or polymers with a branched or crosslinked, linear or cyclic structure, of variable molecular weight, obtained by polymerization and/or polycondensation of suitably functionalized silanes, and essentially consisting of a repetition of principal units in which the silicon atoms are linked to each other by oxygen atoms (siloxane bond), optionally substituted hydrocarbon radicals being directly linked, via a carbon atom, to the said silicon atoms. The most common hydrocarbon radicals are alkyl, and in particular methyl, radicals, fluoroalkyl radicals, aryl, and in particular phenyl, radicals, and alkenyl, and in particular vinyl, radicals. Other types of radicals capable of being linked, either directly or via a hydrocarbon radical, to the siloxane chain are in particular hydrogen, halogens and in particular chlorine, bromine or fluorine, thiols, alkoxy radicals, polyoxyalkylene (or polyether) and in particular polyoxyethylene and/or polyoxypropylene radicals, hydroxyl or hydroxyalkyl radicals, substituted or unsubstituted amino groups, amide groups, acyloxy or acyloxyalkyl radicals, hydroxyacylamino or aminoalkyl radicals, quaternary ammonium groups, amphoteric or betaine groups, anionic groups such as carboxylates, thioglycolates, sulpho-succinates, thiosulphates, phosphates and sulphates, this list of course not at all being limiting (so-called "organomodified" silicones).

In general, the silicones which can be used in the context of the present invention are those which are in particular described in "Encyclopedia of Chemical Technology, Kirk-Othmer, Third Edition, volume 20, pages 922 and subsequent pages" and in "Chemistry and Technology of Silicones, Walter NOLL, Academic Press Inc, San Diego, California, 1968".

The average molecular weight of the silicones which can be used according to the invention can vary between 100 and several millions, preferably between 1000 and 1,000,000.

According to the present invention, it is of course possible to either use only one and the same silicone, or to use several different silicones.

By way of examples of silicones which can be used in the dispersions according to the invention, there may be mentioned in particular polydialkyl-siloxanes, polyalkylarylsiloxanes, polydiaryldialkyl-siloxanes, and still more generally all the polyalkylarylsiloxanes described in the patent application published under the number WO 93/05762.

According to a particularly preferred embodiment of the present invention, the silicones used are chosen from diorganopplysiloxanes (oils, gums or resins), preferably polydialkylsiloxanes or polyalkyl-arylsiloxanes, and still more preferably polydimethyl-siloxanes which are optionally modified.

The silicone gums are particularly preferred, and in particular the polydialkylsiloxane or polyalkyl-arylsiloxane gums which are optionally modified. They can be used alone or in the form of a mixture in a solvent chosen for example from volatile silicones, polydimethylsiloxane or polyphenylmethylsiloxane oils, isoparaffins, pentane, dodecane or mixtures thereof.

The silicone(s) are present in the dispersions in accordance with the invention in proportions generally of between 0.05 and 10% by weight, preferably from 0.1 to 3% by weight, relative to the total weight of the dispersion.

The compositions according to the invention may also comprise all adjuvants conventionally used in compositions, provided that the resulting compositions satisfy the test defined above.

Thus, the compositions according to the invention may contain surfactants, preservatives, sequestrants, emollients, perfumes, colorants, viscosity-modifying agents, foam-modifying agents, antifoams, pearlescent agents, moisturizing agents, antidandruff agents, antiseborrhoeic agents, sunscreens, proteins, vitamins, plasticizers, hydroxy acids, electrolytes and perfumes.

The cosmetically acceptable aqueous or aqueous-alcoholic medium serving as carrier for the compositions according to the invention preferably consists of water or an aqueous-alcoholic solution consisting of water and one or more monoalcohols such as for example lower alcohols such as ethanol, isopropanol or butanol, one or more polyalcohols, one or more glycol ethers which may be used alone or in the form of a mixture.

Still more preferably, the said carrier essentially consists of water.

The compositions according to the invention may also contain conditioning agents which may be chosen from oils and waxes, which are natural or synthetic, fatty alcohols, esters of polyhydric alcohols, glycerides, silicone gums and resins or mixtures of these different compounds.

The compositions according to the invention are more particularly hair-setting lotions, blow-drying lotions, fixing compositions (lacquers) and hair-styling compositions, mousses or gels. The lotions may be packaged in various forms, in particular in vaporizers, pump dispensers or in aerosol containers in order to ensure application of the composition as a spray.

When the composition according to the invention is pressurized in aerosol form, the aerosol comprises the composition described above, called juice, and at least one propellent which may be chosen from volatile hydrocarbons such as n-butane, propane, isobutane, pentane, chlorinated and/or fluorinated hydrocarbons and mixtures thereof. It is also possible to use as propellent carbon dioxide, nitrous oxide, dimethyl ether, nitrogen, compressed air and mixtures thereof.

In such a system, the concentration of propellent(s) is generally between 10 and 50% by weight relative to the total weight of the pressurized composition and preferably between 15 and 35% by weight.

The propellents are generally present in the mousses in proportions of less than 25% by weight relative to the total weight of the composition and preferably in proportions of between 1% and 10% by weight.

The subject of the invention is also a method of cosmetic treatment of keratinous fibres, such as hair, characterized in that it consists in applying to the keratinous fibres, in particular by spraying or vaporizing, a cosmetic composition as defined above, and then in optionally rinsing/with water, after an optional exposure time.

In the examples which follow, all the proportions, unless otherwise stated, are expressed by weight, and AM means active material.

The mean sticking energy was determined as indicated in the test above, for different compositions containing at least one aqueous dispersion of fixing polymer, as well as the percentage of keratinous fibres with a sticking energy greater than 200 $\mu J$.

The compositions of the aqueous dispersions as well as the results of the tests are indicated in Table I below.

TABLE I

| Aqueous dispersion of polymer material (diluted in water containing 10% AM) | Mean sticking energy ($\mu J$) | Percentage of hair with elastically deformed hair Sticking energy greater than 200 $\mu J$ | Composition according to the invention |
|---|---|---|---|
| SANCURE 815 | 1809 | 85.7 | NO |
| DYFLEX LP9636 plasticizer (20%) | 1624 | 82.3 | NO |
| DYFLEX LP9661 | 1438 | 55 | NO |
| AMERHOLD DR25 | 222 | 15.9 | NO |
| AMERHOLD DR25 + polymer A | 868 | 66.6 | NO |
| AMERHOLD DR25 + Y 14143 | 416 | 0 | NO |
| AMERHOLD DR25 (6% AM) + polymer B | 65 | 4 | YES |
| AMERHOLD DR25 (10% AM) + SLM 23 105 (1% AM) | 32 | 0 | YES |

| | |
|---|---|
| SANCURE 815 | Aliphatic polyurethane as a 30% dispersion in a water/N-methyl pyrrolidone/triethylamine mixture, marketed by SANNCOR INDUSTRIES. |
| DYFLEX LP9636 | Butyl methacrylate/methyl methacrylate/butyl acrylate/acrylic acid copolymer as a 42% anionic emulsion, marketed by DYFLEX POLYMERS |
| DYFLEX LP9661 | Acrylic acid/polyacrylate copolymer as a 42% anionic emulsion, marketed by DYFLEX POLYMERS. |
| AMERHOLD DR25 | Methacrylic acid/acrylic acid/ethyl acrylate/methyl methacrylate copolymer as a 25% aqueous dispersion, marketed by AMERCHOL. |
| POLYMER A | Vinyl acetate/vinyl p-tert-butyl-benzoate/crotonic acid (65/25/10) terpolymer. |
| SILSOFT A-843 | Polydimethylsiloxane/amino-polyether (80/20) block copolymer as a 30% solution in dipropylene glycol, marketed by OSI. |
| POLYMER B | Methyl methacrylate/methacrylic acid/dimethacrylate of ethylene glycol (91/5/4). |
| SLM 23105 | Polydimethylsiloxane containing $\alpha$, $\omega$-succinic groups neutralized with aqueous ammonia, as a 23% nonionic aqueous emulsion, marketed by WACKER. |

Only the last two compositions of Table I which satisfy the invention exhibit good performance in retaining the hairstyle while avoiding the drawbacks of removal during brushing.

What is claimed is:

1. A cosmetic composition comprising at least one aqueous dispersion of insoluble particles of fixing polymer, wherein said composition has a mean sticking energy of less than 200 microjoules, and further wherein said mean sticking energy of said composition to keratinous fibers results from drying said composition to said keratinous fibers.

2. A composition according to claim 1, wherein said composition is in a cosmetically acceptable medium chosen from aqueous and aqueous alcoholic media.

3. A composition according to claim 1, wherein said mean sticking energy is less than 200 microjoules for more than 85% of the fibres.

4. A composition according to claim 1, wherein said at least one aqueous dispersion of insoluble particles of fixing polymer results from the polymerization of at least one monomer chosen from styrene, butadiene, ethylene, propylene, vinyltoluene, vinyl propionate, vinyl alcohol, acrylonitrile, chloroprene, vinyl acetate, urethanes, isoprene, isobutene, vinyl ether, vinyl-pyrrolidone, vinyl imidazole, acids chosen from acrylic, methacrylic, maleic, crotonic and itaconic acids, esters of acrylic, methacrylic, maleic, crotonic and itaconic acids, and amides of acrylic, methacrylic, maleic, crotonic and itaconic acids.

5. A composition according to claim 1, wherein said fixing polymer is chosen from ethyl acrylate/methyl methacrylate/methacrylic acid/acrylic acid copolymers.

6. A composition according to claim 1, wherein said composition is pressurized as an aerosol and further comprises at least one propellent.

7. A composition according to claim 1, wherein said mean sticking energy is less than 100 microjoules.

8. A composition according to claim 7, wherein said mean sticking energy is less than 100 microjoules for more than 85% of the fibres.

9. A composition according to claim 1, wherein said composition further comprises a plasticizer.

10. A composition according to claim 9, wherein said composition after drying possesses a glass transition temperature ranging from 20 to 40° C.

11. A composition according to claim 1, wherein said composition further comprises at least one silicone.

12. A composition according to claim 11, wherein said at least one silicone is chosen from silicone oils, silicone gums and silicone resins.

13. A composition according to claim 11, wherein said at least one silicone is present in an amount ranging from 0.05 to 10% relative to the total weight of the composition.

14. A composition according to claim 11, wherein said at least one silicone is present in an amount ranging from 0.1 to 3% relative to the total weight of the composition.

15. A method of cosmetically treating keratinous fibres comprising applying to said keratinous fibers a composition which comprises at least one aqueous dispersion of insoluble particles of fixing polymer, wherein said composition has a mean sticking energy of less than 200 microjoules, and further wherein said mean sticking energy of said composition to said keratinous fibers results from drying to said keratinous fibers.

16. A method according to claim 15, wherein said keratinous fibers are hair.

17. A method according to claim 15, wherein said applying of said composition to said keratinous fibers comprises spraying or vaporizing said composition.

18. A hair-setting lotion, blow-drying lotion, lacquer, mousse or gel comprising at least one aqueous dispersion of insoluble particles of fixing polymer, wherein said hair-setting lotion, blow-drying lotion, lacquer, mousse or gel has a mean sticking energy of less than 200 microjoules, and further wherein said mean sticking energy of said hair-setting lotion, blow-drying lotion, lacquer, mousse or gel to keratinous fibers results from drying said hair-setting lotion, blow-drying lotion, lacquer, mousse or gel to said keratinous fibers.

19. A method of improving the capacity for removal of a composition by brushing comprising including in said composition another composition which comprises at least one aqueous dispersion of insoluble particles of fixing polymer, wherein said composition has a mean sticking energy of less than 200 microjoules, and further wherein said mean sticking energy of said composition to said keratinous fibers results from drying to said keratinous fibers.

* * * * *